United States Patent [19]

Traitler et al.

[11] Patent Number: 5,011,855

[45] Date of Patent: Apr. 30, 1991

[54] COSMETIC AND DERMATOLOGICAL COMPOSITIONS CONTAINING γ-LINOLENIC ACID

[75] Inventors: Helmut Traitler; Heike Winter, both of Vevey, Switzerland

[73] Assignee: Nestec S. A., Vevey, Switzerland

[21] Appl. No.: 348,712

[22] Filed: May 8, 1989

Related U.S. Application Data

[60] Division of Ser. No. 542,149, Oct. 14, 1983, Pat. No. 4,703,060, which is a continuation-in-part of Ser. No. 482,429, Apr. 6, 1983, abandoned.

[51] Int. Cl.$^5$ .............................................. A61K 31/20
[52] U.S. Cl. ..................................... 514/558; 424/74; 424/195.1; 514/844
[58] Field of Search ...................... 424/74, 195.1, 549, 424/558; 514/844

[56] References Cited

U.S. PATENT DOCUMENTS

| 4,569,839 | 2/1986 | Grollier et al. | 424/74 |
| 4,767,618 | 8/1988 | Grollier et al. | 424/74 |

FOREIGN PATENT DOCUMENTS

| 1603383 | 5/1971 | France . |
| 2197605 | 3/1974 | France . |
| 2255055 | 7/1975 | France . |
| 1240513 | 7/1971 | United Kingdom . |
| 1446431 | 8/1976 | United Kingdom . |

OTHER PUBLICATIONS

French translation of Hungarian Patent No. T13226.

*Primary Examiner*—John W. Rollins
*Attorney, Agent, or Firm*—Vogt & O'Donnell

[57] ABSTRACT

Cosmetic and dermatological compositions containing from 1% to 30% by weight of an oil extracted from pips of Ribes genus fruits containing at least 4% by weight of γ-linolenic acid are provided. The oil is substantially free from waxes, odorous compounds, colorings and free fatty acids.

9 Claims, No Drawings

COSMETIC AND DERMATOLOGICAL COMPOSITIONS CONTAINING γ-LINOLENIC ACID

CROSS-REFERENCE TO RELATED APPLICATIONS

This is a divisional application of application Ser. No. 06/542,149, filed on Oct. 14, 1983, now U.S. Pat. No. 4,703,060, which, is a continuation-in-part application of Application Ser. No. 06/482,429, filed on Apr. 6, 1983, now abandoned.

BACKGROUND OF THE INVENTION

1. Field of the Invention

This invention relates to nutritive compositions containing fatty substances, and to a process for the preparation of said compositions from fruits of the Ribes genus.

2. Description of Related Art

Most vegetable oils contain linolenic (6,9-octadecadienic) and α-linolenic (9,12,15-octadecatrienic) polyunsaturated fatty acids. Only oils of the seeds of hops (Humulus), of hemp (Cannabis), of borage (Borage) and of evening primrose (Oenothera) are known as containing γ-linolenic (6,9,12-octadecatrienic) acid, evening primrose being the only available source at, moreover, a high price.

γ-Linolenic acid is an essential fatty acid which is metabolised by the organism into prostaglandins via dihomo-γ-linolenic acid and arachidonic acid (5,8,11,14-eicosatetraenic), which is itself a constituent of cellular membranes, whereas α-linolenic acid does not take part in the same way in this metabolic process. The linoleic acid conversion into γ-linolenic acid in the tissue is incomplete (4–20% compared to 90–98% for the conversion of γ-linolenic acid into arachidonic acid) and may not even exist (for example in cats) in the case of the absence or the inactivation of the enzyme Δ-6-desaturase.

In effect, a lack of essential fatty acids results in a nutritional deficiency affecting all the metabolic processes which have been mentioned above and which may result in biochemical disorders or in organic lesions (for example coagulation disorders, dermatological lesions, endocrinal complaints, myocardiac lesions, and hepatic, articular, neurological and mental disorders). Therefore, it is possible to see the advantages provided by a supply of γ-linolenic acid for the prevention or for the treatment of these anomalies.

The possibility of using γ-linolenic acid and arachidonic acid as therapeutic and nutritional agents has been mentioned in, for example French Patents Nos. 2,197,605 and 1,603,383, γ-linolenic acid being of a synthetic origin or being extracted from the oil of evening primrose (Oenothera) or officinal borage (Borage officinalis) seeds.

Moreover, French Patent No. 2,255,055 relates to cosmetic or pharmaceutical compositions based on the oil of raspberry pips, the anti-inflammatory activity of which is mentioned, but with no indication of the composition. Since the oil is preferably extracted using chloroform (a polar solvent), the anti-inflammatory activity is probably due to the presence of minor components. Moreover, analysis of this oil has shown that it contained about 54% by weight of linoleic acid and 30% of a α-linolenic acid, but did not contain any γ-linolenic acid.

Finally, Hungarian Patent No. T 13226 states that the addition of a pulp or a crude oil extracted from paprika, tomato or redcurrant pips to cosmetic products or table oils would inhibit their oxidation. The extraction, as it is described, does not allow the separation of the undesirable waxes and colourings in the products which are envisaged and the composition of the extract is not mentioned.

SUMMARY OF THE INVENTION

Surprisingly, it has been found that oils of pips of fruit of the Ribes genus contain an appreciable percentage, at least 4% by weight, of γ-linolenic acid. Moreover, these pips are available in large quantities in the cakes resulting from squeezing fruit juices, from the production of preserves and jellies or from fermentation musts resulting from the production of brandies, liqueurs and schnapps, by-products which have been used up until now as fuel or forage.

The present invention relates to nutritive compositions which contain from 1 to 80% by weight of a fatty substance extracted from pips of fruit of the Ribes genus containing at least 4% by weight of γ-linolenic acid which is practically free from odorous compounds, the free fatty acids, the colourings and the waxes of these fruits.

DESCRIPTION OF THE INVENTION

As used in the context of this invention, the term "nutritive composition" designates cosmetic, dermatological (corrective cosmetic) or topical (for example ophthalmic) compositions and dietetic foods or food supplement, or pharmaceutical compositions for oral, enteral or parenteral nutrition.

According to the present invention, the fatty substances entering into the nutritive composition originate in practice from blackcurrants (*Ribes nigrum*), redcurrants (*Ribes rubrum*), gooseberries (*Ribes ovacrispa* or *grossularia*) or from hybrid fruits of these species. Of course, a mixture of these fruits may be used.

The lipid content of the by-products mentioned above is from 12 to 30% by weight, depending on the starting material. For its part, the lipid phase contains from 4 to 19% by weight of γ-linolenic acid.

As an indication, the oil of the pips of these fruits comprises triglycerides of the following fatty acids, by weight:

| Fatty Acids | Blackcurrants | Red Currants | Gooseberries |
| --- | --- | --- | --- |
| C 16: 0 | 6–7% | 4–5% | 7–8% |
| C 18: 0 | 1–2% | 1–2% | 1–1% |
| C 18: 1 cis | 9–10% | 14–15% | 15–16% |
| C 18: 1 trans | 0.5% | 0.5–1% | 1–2% |
| C 18: 2ω6 | 47–49% | 41–42% | 39–41% |
| C 18: 3ω6 | 15–19% | 4–5% | 10–12% |
| C 18: 3ω3 | 12–14% | 29–31% | 19–20% |
| C 18: 4ω3 | 3–4% | 2.5–3.5% | 4–5% |

Blackcurrant oil which is preferred due to its high content of γ-linolenic acid also contains from 1 to 2% by weight of unsaponifiable substances, such as aliphatic alcohols, hydrocarbons, tocopherols, squalene, β-sitosterol, campesterol and Δ-7 stigmasterol. Its density is 0.9215 g/cm$^3$ (at 20° C.), and its viscosity is 28.3 centipoise (at 20° C.).

A cosmetic or dermatological composition may be presented in the form of a fluid water-in-oil or oil-in-water emulsion (milk, lotion, shampoo, shaving foam, etc.,) or in the form of a thicker emulsion (cream, face pack), and it generally contains from 1 to 20% by weight of the fatty substance mentioned above. It may essentially comprise an oil phase (balm, bath oil, etc.), containing up to 80% of the fatty substance mentioned above, or it may have a predominant water phase (capillary rinsing product, etc.). Finally, it may be essentially solid (make-up products, eye shadow, foundation, lipstick, etc.) and may contain from 1 to 30% of the fatty substance mentioned above.

In addition to containing the fatty substance mentioned above, the fat phase of the composition may contain vegetable, animal, mineral or synthetic oils, waxes, long chain alcohols and polymers which are presently used in cosmetics.

If emulsions are concerned, the compositions contain from 1 to 20% by weight of emulsifiers.

Moreover, the compositions may contain colouring agents, perfumes, preservatives, pigments, lustrants, antioxidants and extenders.

Among the dietetic foods or food supplements which are envisaged, it is possible to mention infants' milk and more particularly milk having the composition of mother's milk, sauces, mayonnaise and oils for salads. In these products, the fatty substances are compounded so that they provide the equivalent of from 0.35 to 2.5% by weight of $\gamma$-linolenic acid and represent from 2 to 15% by weight. The fatty substances will advantageously be protected from oxidation by the addition of fatty acid esters of ascorbic acid, for example, ascorbyl palmitate.

It is also possible to envisage using the fatty substances mentioned above in animal nutrition, particularly in feeds, for example, meat compositions for cats.

Finally, the fatty substances mentioned above may enter into the composition of medicaments which have a formulation adapted to the method of administration and are administered, for example, in the form of a syrup or capsules or ocular isotonic emulsions, or they may be constituents of the oil phase of emulsions or combined with oils intended for parenteral nutrition, and they may represent from 5 to 80% by weight of the composition.

In every case, the pharmaceutical compositions according to the present invention will be stabilised physically and chemically (in particular against oxidation) and those for parenteral use presented in sterile, pyrogen-free form.

The present invention also relates to a process for the preparation of fatty substances from pips of fruit of the Ribes genus, characterised in that a vegetable material containing these pips is either ground and extracted by solvents or, alternatively, is pressed and/or extracted by solvents in order to obtain a fatty substance containing at least 4% by weight of $\gamma$-linolenic acid which is practically free from the odorous compounds, the free fatty acids, the colourings and the waxes of these fruits.

According to the present invention, the term "vegetable material" which is used is understood as designating the by-products which have been mentioned above. The starting material is generally in the form of strongly coloured cakes containing the waxes associated with the pips, waxes and colourings representing from 5 to 7% by weight of the crude oil which would be extracted therefrom, for example, using hexane. The waxes are saturated and mono-unsaturated esters of long chain fatty acids with fatty alcohols which are solid at ambient temperature. The waxes and colourings in question are not desired in an oil incorporated in nutritive compositions.

A preferred starting material is the cake obtained by squeezing fruit juices, in particular blackcurrant juice. The cake is initially dried, for example, in air for about 1 hour at about 60° C. It is coarsely ground and sieved in order to obtain particles of from 1 to 1.5 mm, the sieving yield ranging from 60 to 80% by weight of the cakes. It is possible to separate advantageously the pips from the chaff by gravity in a flow of air or by elutriation with a yield by weight of from 80 to 90%.

According to a preferred embodiment of the present process, the pips are washed with a conventional polar solvent in order to free them from waxes, colourings and free fatty acids. For cosmetic uses, it is possible to use, for example methanol, isopropanol, acetone, ethanol or a mixture of these solvents, or a supercritical fluid, for example, carbon dioxide under conditions which impart thereto a polar character. For nutritional and pharmaceutical uses, a food-grade solvent will be used, for example, ethanol or supercritical carbon dioxide.

By way of example, washing is carried out by extracting the pips with a polar solvent, such as ethanol, under reflux, either in batches, for example, at first for about 2 hours and then for about 30 to 60 minutes, or continuously for about 2 hours, then the residue is drained.

In a variant, it is possible to wash the pips using a supercritical fluid in a polar condition, for example, carbon dioxide under from 250 to 350 bars and at 60 to 80° C. in a continuous cycle, the solvent being recovered in gas form by lowering the pressure, then being recompressed and recycled.

It has been found that washing makes it possible to remove most of the colouring materials and the waxes present in the skins and around the pips. In effect, the waxes are precipitated on cooling from the polar solvent solution, whereas the said polar solvent solution is very strongly coloured.

A variant of the separation and cleaning of pips from the fruit juice press cakes comprises treating the cakes enzymatically, for example, with an aqueous solution containing 0.01 to 0.5% by weight of cellulase at a pH of from 4 to 5 and at a temperature of from 38 to 42° C for 1 to 4 hours or at ambient temperature for from 12 to 15 hours. The pips can easily be separated from the slurry and both waxes and colourings are at least partly eliminated in this manner.

Regardless of which variant is employed to obtain the pips, it is advantageous to treat the washed and drained pips with an antioxidant. This treatment protects the oil contained therein against oxidation in the subsequent stages. Suitable antioxidants include, for example, aqueous dilute solutions of ascorbic or benzoic acids or sodium or potassium salts of these acids, or combinations thereof, ascorbic acid being preferred.

The protected pips containing the antioxidant may then be pressed, for example, in a continuous screw press at high pressure. Depending on the type of press used, the number of pressing cycles, and the pressing conditions applied, up to 90% of the oil may be recovered.

In a variant, the pips are extracted with a solvent. Prior to solvent extraction, the drained residue is ground (particles of from 100 to 300$\mu$m), from about 10 to 15% by weight of water is added, and it is then made into pellets or granules by extruding the paste and cutting the strand. In a still further variant, it is possible to flake the pips on a flattening cylinder from the non-ground drained residue. These forms prevent clogging and facilitate the subsequent extraction of the oil by providing the product with a porosity permitting a good penetration of the solvent, and the flakes in particular resist crushing.

A preferred variant of this stage comprises flaking the protected pips and pressing the flakes prior to solvent extraction. The protected pips are dried, flaked, and the flakes are preheated at a temperature of from 80° to 90° C. and pressed at a pressure of from 500 to 800 kg/cm$^2$, the press head temperature being kept under 90° C. In this way, about 50 to 60% of the oil present in the pips are obtained. The resulting press cake has a density of from 0.58 to 0.65 g/cm$^3$, about twice the density of the flakes. This is recommended for a good percolation of the solvent. The press cake is then milled and subjected to solvent extraction.

The next stage comprises extracting the oil with a non-polar solvent, for example, hexane, preferably under reflux in a proportion of from 200 to 250% by weight of hexane with respect to the residue. The non-polar solvent is preferably separated from the oil by evaporation. In a variant, it is equally possible to use in this stage liquid carbon dioxide or preferably supercritical carbon dioxide under conditions in which it is slightly polar, for example, under from 200 to 300 bars and at 40° to 60° C. Of course, it is possible to use, for example, a supercritical fluid preferably carbon dioxide in the washing stage and in the subsequent extraction stage, or in only one of these stages, the other being carried out using, for example, ethanol or hexane. In the extraction stage, as above with the washing stage, the supercritical fluid solvent is separated by recovering it in gas form by lowering the pressure and then recompressing it, and it may then be recycled.

After extraction, it is possible, although these measures are only preferred options, to neutralize the solution to remove the residual free fatty acids, after having partially evaporated the solvent, for example in the case of hexane, so that it contains about 80% to 90% by weight of solvent and 10% to 20% by weight of oil, using a concentrated alkali such as (2N) concentrated potassium or sodium hydroxide, to cool the solution to about 0° to 4° C. for about 24 hours and to filter it at this temperature in order to completely remove the residual waxes. Likewise, the subsequent decolorization and deodorization operations are preferred options: the solution is decolorized using 2 to 8% by weight of an adsorbent, for example, active carbon or activated aluminum silicate such as bentonite or montmorillonite with respect to the oil treated, at from 20° to 60° C., then the hexane is evaporated. The oil is then deodorized by steam stripping at from 140° to 220° C. and preferably at about 180° C. under a vacuum equal to or less than 1 torr.

According to one variant for the preparation of the oil, the pips, which have been ground are not previously washed, but are directly extracted with a non-polar solvent. In this case, the neutralization, the removal of the waxes by decantation, the decolorization and the deodorization as indicated above are essential for the production of a pale yellow refined oil.

In some cases, a fatty substance is to be enriched with γ-linolenic acid. In order to do this, the oil which is freed from waxes and free fatty acids is saponified with an alkali hydroxide, for example, potassium hydroxide in a medium of methanol/water in a concentration of about 11%, the resulting salts are acidified using a mineral acid, for example 2N sulphuric acid, the free fatty acids are extracted with a non-polar solvent, for example, hexane, and the organic phase is separated and dried, for example, by the addition of sodium sulphate. In a variant, it is possible to directly treat the ground cake with an alkali hydroxide, to acidify it using a mineral acid, to extract the free fatty acids with hexane and to dry the organic phase as indicated above. The organic phase is fractionated by high pressure chromatography in liquid phase, by passage over columns of silica gel loaded with silver cations such as by utilizing silver nitrate and elution preferably with a mixture of dichloromethane, toluene and diethyl ether 70:25:5–65:30:5 in isocratic manner, i.e., with recycling of the solvent mixture of fixed composition, and a fraction containing about 60% by weight of γ-linolenic acid and about 40% of α-linolenic acid is thus obtained.

Practically pure γ-linolenic acid may be isolated from the fraction obtained from the dried organic phase by high pressure liquid phase chromatography with a $C_8$ or $C_{18}$ support in inversed phase with a solvent gradient such as by a solvent mixture of acetonitrile/water, methanol/water or isopropanol/water.

The following examples illustrate the present invention. In these Examples, the parts and percentages are based on the weight.

EXAMPLE 1

100 kg of residue obtained by the extraction of blackcurrant juice and drying are treated a first time for 2 hours under reflux with 250 kg of ethanol and a second time for 1 hour under reflux with 250 kg of ethanol. The extract is drained and is dried twice at 80° C. over a period of 30 minutes in an air drier, and is finally ground in a hammer mill.

After moistening with from 10 to 15% of water and after extruding the paste in the form of pellets, the 89 kg of product which is obtained are extracted twice with 205 kg of hexane under reflux for 3 hours, then cooled and filtered. The hexane is then evaporated and 14.3 kg of a clear yellow oil are obtained, the weight content of free fatty acids of which is 0.16%.

EXAMPLE 2

100 kg of dried residue resulting from the extraction of blackcurrant juice are ground in a hammer mill, and the powder is sieved in order to obtain particles of from 1 to 1.5 mm with a sieving yield of from 60 to 80%. The product is moistened and made into pellets and then extracted with hexane, as in Example 1. Part of the hexane is evaporated, the free fatty acids are neutralized with a 2N solution of sodium hydroxide, the organic phase is separated, is left to settle at 4° C. for 24 hours and is separated by filtration from the hard waxes which have settled. The organic phase is treated with from 2 to 8% of active carbon based on the quantity of oil in solution, then the solvent is evaporated and the oil is deodorized by stripping with steam at 180° C. under a vacuum of 0.1 torr. From 13 to 16 kg of refined oil are thus obtained.

EXAMPLE 3

100 kg of dried blackcurrant pulp resulting from juice squeezing are ground in a disc mill and the ground product is sieved in order to obtain 60.5 kg of particles of from 1 to 1.5 mm. The product is introduced into an elutriator and 49.5 kg of a heavy fraction essentially comprising seeds are recovered. The fraction is washed twice with each time 120 kg of ethanol under reflux. The process is continued as stated in Example 1, except that two times 120 kg of ethanol are used for the washing operation, the dried extract is made into flakes using a flattening cylinder mill instead of the extruder, and the flakes are extracted with two times 102.5 kg of hexane. 11.1 kg of a clear, yellow oil are obtained.

EXAMPLE 4

200 kg of ethanol washed blackcurrant pips obtained as stated in Example 3 are sprayed with 14 to 16 liters of water containing 30 to 50 ppm (parts per million) of ascorbic acid. The treated pips are dried at about 70° C. for 30 to 40 min. and subsequently flaked. The flakes are then heated in a toaster at 80° to 90° C. for 30 to 40 min. Their density is about 0.35 g/cm$^3$. The flakes are pressed for 30 to 50 min. in a continuous screw press under a pressure of from 500 to 800 kg/cm$^2$, at a rotational speed of the screw of 10 to 20 RPM, the press head temperature being kept at 80° to 90° C. Under these conditions, 26 to 31 kg of oil (about 50 to 60 % of total oil present in the seeds) are obtained. The press cake has a density of about 0.60 g/cm$^3$ which is quite suitable for percolation of the solvent during the subsequent solvent extraction. It is then milled and subjected twice to hexane extraction, as stated in Example 3, with 370 to 400 kg of hexane under reflux for 3 hours, then cooled and filtered. The hexane is then evaporated and 22 to 26 kg of additional oil are obtained.

|  | % by weight |
|---|---|
| EXAMPLES 5 to 15: COSMETIC COMPOSITIONS | |
| 5 - Care cream (water-in-oil emulsion) | |
| Isopropyl myristate | 30 |
| Liquid paraffin | 18 |
| Blackcurrant oil | 10 |
| Ozokerite | 4 |
| Magnesium lanolate | 14.4 |
| Lanolin alcohol | 3.6 |
| Butyl hydroxy anisole (BHA) + butyl hydroxy toluene (BHT) | 0.01 |
| Water + preservative:quantity sufficient for | 100% |
| 6 - Body Milk | |
| Liquid paraffin | 8 |
| Blackcurrant oil | 3 |
| Glycerol stearate | 2 |
| Tween 60 (polyoxyethylene) (20) sorbitan monostearate | 1 |
| Stearic acid | 1.4 |
| Triethanolamine | 0.7 |
| Carbopol 940 (neutralized) | 0.2 |
| BHA + BHT | 0.01 |
| Perfume | 1 |
| Water + preservative quantity sufficient for | 100% |
| 7 - Balm | |
| Ozocerite | 4 |
| Blackcurrant oil | 12 |
| Miglyol gel | 30 |
| Vaseline | 20 |
| Soya oil | 15 |
| Sunflower seed oil | 19 |
| 8 - Body Oil | |
| Blackcurrant oil | 30 |
| Soya oil | 10 |
| Sunflower seed oil | 30 |
| Peanut oil | 29.8 |
| BHA + BHT | 0.2 |
| 9 - Face pack | |
| Blackcurrant oil | 10 |
| Cetyl alcohol | 3 |
| Stearyl alcohol | 3 |
| Polyoxyethylene (20) sorbitan mono-oleate (Polysorbate 80) | 4 |
| 1,2-propylene glycol | 5 |
| Glycerol | 2 |
| Titanium dioxide | 3.5 |
| Preservative | 0.3 |
| Distilled water, perfume concentrate antioxidant (BHA + BHT) quantity sufficient for | 100% |
| Plant extracts or biological extracts may be added as desired | |
| 10 - Shaving cream | |
| Blackcurrant oil | 9.4 |
| Stearic acid | 7 |
| Cetyl alcohol | 0.7 |
| Polyethylene glycol monostearate | 3.5 |
| BHA + BHT | 0.05 |
| Glycerol | 9 |
| Preservative | 0.3 |
| Triethanolamine | 2.7 |
| Perfume and water quantity sufficient for | 100% |
| 11 - Eye shadow | |
| Talc | 50 |
| Wheat starch | 12 |
| Zinc stearate | 3 |
| Ultramarine blue | 4.5 |
| Yellow iron oxide | 3.2 |
| Black iron oxide | 0.5 |
| Brown iron oxide | 0.8 |
| Chromium oxide | 2.5 |
| Titanium mica | 10 |
| Titanium mica + iron oxide | 3.5 |
| Agglomerating agent | 10 |
| Formula of the agglomerating agent: | |
| Liquid paraffin | 50 |
| Liquid lanolin | 20 |
| Blackcurrant oil | 20 |
| Glycerol monstearate | 9 |
| Propyl parahydroxy benzoate | 0.5 |
| BHA + BHT | 0.5 |
| 12 - Lipstick | |
| White base: | |
| Petroleum ceresin | 12 |
| Cadelilla wax | 2 |
| Synthetic heavy esters (Croda Synchro wax ERLC) | 4 |
| Castor oil | 10 |
| Blackcurrant oil | 15 |
| Isopropyl lanolate | 15 |
| Liquid lanolin | 10 |
| Acetylated lanolin | 12 |
| Vaseline | 10 |
| Cetyl ricinoleate | 9.8 |
| BHA + BHT (50/50) | 0.2 |
| to which are added 5.4 parts by weight of the following pigments for 100 parts by weight of white base: | |
| Organic and mineral pigments: | |
| Red iron oxide | 1.2 |
| Titanium oxide | 1.3 |
| D and C red No 9 | 2 |
| D and C red No 27 | 0.4 |
| Perfume | 0.5 |
| 13 - Foundation (water-in-oil emulsion) | |
| Oil phase: | |
| Liquid paraffin | 5 |
| Blackcurrant oil | 5 |
| Shorea fat | 4 |
| Perhydrosqualene | 6 |
| Ozokerite | 2 |
| Magnesium lanolate | 5 |
| Lanolin alcohol | 3 |

-continued

| | % by weight |
|---|---|
| Iron oxide | 3 |
| Titanium dioxide | 4 |
| Polyethylene | 10 |
| Perfume | 0.4 |
| BHA + BHT | 0.5 |
| Water + preservative:quantity sufficient for | 100% |

14 - Baby bath oil

| | |
|---|---|
| Blackcurrant oil | 20 |
| Oleic alcohol polyglycol ether | 15 |
| Medium chain triglycerides ($C_8$–$C_{10}$) | 15 |
| Isopropyl myristate | 30 |
| Octyl palmitate | 10 |
| Antioxidant (BHA + BHT) and perfume: quantity sufficient for | 100% |

15 - Hair rinse

The following composition is prepared:

| | |
|---|---|
| Stearyl alcohol | 1.8 |
| Cetylstearyl alcohol with 15 mols of E.O.* | 5.6 |
| Blackcurrant oil | 2.5 |
| Quaternised cellulose sold under the name JR 400 by Union Carbide | 0.8 |
| Water quantity sufficient for | 100.0% |

This composition is applied after the hair has been washed and is left on for 5 minutes. The hair is then rinsed. Wet hair is easy to comb out and the clean head of hair is soft and silky.

*Ethylene oxide

EXAMPLES 16 TO 18: DIETETIC FOODS

16 - Dressing for salads

| | |
|---|---|
| Blackcurrant oil | 10 |
| Grape pip oil | 14.5 |
| White vinegar | 3.2 |
| Red vinegar | 4.4 |
| Mustard powder | 5.35 |
| Onion powder | 0.25 |
| Salt | 1.4 |
| Sugar | 1 |
| Emulsifier | 2.5 |
| Preservative (ascorbyl palmitate) | 0.1 |
| Powdered egg | 4.2 |
| Water | 53.1 |

7 - Oil for salads

| | |
|---|---|
| Blackcurrant oil | 10 |
| Grape pip oil | 90 |

8 - Infant's milk

| | |
|---|---|
| Blackcurrant oil (corresponds to 0.35% of γ-linolenic acid calculated on the total weight of the fats, which is the amount in human milk) [FATS] | 0.61 |
| Corn oil [FATS] | 2.47 |
| Lactic fat [FATS] | 11.64 |
| Medium chain triglycerides [FATS] | 9.28 |
| Carbohydrates, of which 41.6 of lactose 56.9 and 15.3 of glucose | |
| Proteins, of which 4.4 of casein and of lactoserum proteins | 14.4 |
| Moisture | 3.0 |
| Ash, of which: | 1.7 |
| Calcium | $350 \times 10^{-3}$ |
| Phosphorus | $200 \times 10^{-3}$ |
| Potassium | $370 \times 10^{-3}$ |
| Sodium | $103 \times 10^{-3}$ | and the minimum quantities of the following vitamins and trace elements:

| | |
|---|---|
| Iron | $6.0 \times 10^{-3}$ |
| Copper | $0.3 \times 10^{-3}$ |
| Zinc | $1.8 \times 10^{-3}$ |
| Iodine | $25 \times 10^{-6}$ |
| Folic acid | $80 \times 10^{-6}$ |
| Vitamin C | $200 \times 10^{-3}$ |

-continued

| | |
|---|---|
| Vitamin E | $10 \times 10^{-3}$ |
| Vitamin $B_1$ | $0.35 \times 10^{-3}$ |
| Vitamin $B_2$ | $0.5 \times 10^{-3}$ |
| Vitamin $B_6$ | $0.9 \times 10^{-3}$ |
| Vitamin $B_{12}$ | $1.7 \times 10^{-3}$ |
| Vitamin PP | $5.2 \times 10^{-3}$ |
| Calcium Pantothenate | $2.6 \times 10^{-3}$ |

This powder is prepared as described in U.S. Pat. No. 4,216,236.

EXAMPLES 19 TO 20: PHARMACEUTICAL COMPOSITIONS

19 - Capsules for oral administration

Gelatine capsules are prepared, containing 500 mg of blackcurrant oil corresponding to 80 mg of γ-linolenic acid per capsule.

| 20 - Fruit syrup for internal use | % by weight |
|---|---|
| Blackcurrant oil | 25 |
| Mixture of mono- and diglycerides | 2 |
| Mixture of gums | 0.7 |
| Sugar | 17 |
| Natural mixture of tocopherols (α, β, γ and δ) | 0.1 |
| Preservative, flavourings and water: quantity sufficient for | 100% |

We claim:

1. A cosmetic composition containing from 1% to 30% by weight of an oil extracted from pips of Ribes genus fruits selected from the group consisting of *Ribes nigrum*, *Ribes rubrum*, *Ribes ovacrispa*, *Ribes grossularia*, hybrids thereof and combinations thereof containing at least 4% by weight of γ-linolenic acid and being substantially free from waxes, odorous compounds, colorings and free fatty acids.

2. A composition according to claim 1 wherein the composition is in a form of a solid.

3. A composition according to claim 1 wherein the composition is in a form of an emulsion selected from the group consisting of a water-in-oil emulsion and an oil-in-water emulsion and wherein the composition contains the Ribes oil in an amount of from 1% to 20% by weight.

4. A composition according to claim 1 wherein the composition has an oil phase containing up to 80% of the extracted Ribes oil in the oil phase.

5. A composition according to claim 1 wherein the composition is selected from the group consisting of body milks, lotions, shampoos, shaving foams, care creams, face packs, balms, bath oils, capillary rinsing products, eye shadows, foundations and lipsticks.

6. A composition according to claim 5 further comprising substances selected from the group consisting of vegetable, animal, mineral and synthetic oils, waxes, long chain alcohols and cosmetic polymers.

7. A composition according to claim 6 further comprising substances selected from the group consisting of coloring agents, perfumes, preservatives, pigments, lustrants, antioxidants and extenders.

8. A composition according to claim 5 further comprising substances selected from the group consisting of coloring agents, perfumes, preservatives, pigments, lustrants, antioxidants and extenders.

9. A composition according to claim 1 wherein the oil is extracted from pips of *Ribes nigrum*.

* * * * *

UNITED STATES PATENT AND TRADEMARK OFFICE
CERTIFICATE OF CORRECTION

PATENT NO. : 5,011,855

DATED : April 30, 1991

INVENTOR(S) : Helmut TRAITLER, et al.

It is certified that error appears in the above-identified patent and that said Letters Patent is hereby corrected as shown below:

On the title page, insert the following:

--[30]  Foreign Application Priority Data
   Apr. 16, 1982 [CH] Switzerland..............2314/82--

Signed and Sealed this

Third Day of November, 1992

Attest:

DOUGLAS B. COMER

Attesting Officer        Acting Commissioner of Patents and Trademarks